United States Patent [19]

Berthold

[11] Patent Number: 4,504,424

[45] Date of Patent: Mar. 12, 1985

[54] PROCESS FOR THE PREPARATION OF ARYLHYDRAZINE-N-SULFONIC ACIDS

[75] Inventor: Rüdiger Berthold, Bad Soden am Taunus, Fed. Rep. of Germany

[73] Assignee: Hoechst Aktiengesellschaft, Frankfurt am Main, Fed. Rep. of Germany

[21] Appl. No.: 409,409

[22] Filed: Aug. 19, 1982

[30] Foreign Application Priority Data

Aug. 21, 1981 [DE] Fed. Rep. of Germany ....... 3133100

[51] Int. Cl.³ .......................................... C07C 143/86
[52] U.S. Cl. .................................. 260/513.6; 548/305
[58] Field of Search ..................... 260/513.6; 564/314; 548/305

[56] References Cited

FOREIGN PATENT DOCUMENTS 1026776 4/1966 United Kingdom ................ 564/314

OTHER PUBLICATIONS

Gattermann, Die Praxis des Organischen Chemikers, 33rd Ed., de Gruyter & Co., Berlin, 1948, p. 171.
Houben–Weyl, vol. X/3, pp. 570, 573.

*Primary Examiner*—Nicky Chan
*Attorney, Agent, or Firm*—Curtis, Morris & Safford

[57] ABSTRACT

The invention relates to a process for the preparation of arylhydrazine-N-sulfonic acids by reduction of aryldiazosulfonates with hydrogen in the presence of transition metal catalysts.

10 Claims, No Drawings

PROCESS FOR THE PREPARATION OF ARYLHYDRAZINE-N-SULFONIC ACIDS

Arylhydrazine-N-sulfonic acids can be easily hydrolyzed to the corresponding arylhydrazines and are thus important intermediate products for these compounds which have many uses.

It is known that arylhydrazine-N-sulfonic acids can be prepared by reduction of the corresponding aryldiazosulfonates. According to Trans. Am. electrochem. Soc. 56, 452; C.A. 23 (1929) 3860 this reduction can be carried out with zinc dust in the presence of acid, with tin and hydrochloric acid and also electrochemically on a mercury cathode. In practice, sodium bisulfite is employed for this purpose. However, in this process the sulfite reacts to give the bisulfate or, after neutralization, the sulfate and sulfur dioxide from the sulfite which is employed in excess. Since sulfate attacks the concrete of the clarification plants during effluent treatment, the treatment of the effluents is, of necessity, correspondingly elaborate.

The use of sulfur dioxide as the reducing agent has also already been described (Die Chemie 56 (1943) 233). In spite of good yields, this process has not found use in practice, since it is quite uneconomical, in particular because of its poor space yield. Thus, for one metric ton of phenylhydrazine, with a reaction volume of 113 m$^3$, which corresponds to a vessel volume of about 150 m$^3$, 86 m$^3$ of water must be distilled off.

A further disadvantage of the known process is that substituted arylhydrazines are either not accessible at all or accessible only with poor yields by this process (Houben-Weyl 10/2, 190; J. Am. Chem. Soc. 78 (1956) 5856).

It has now been found that the abovementioned disadvantages are avoided when the aryldiazosulfonates are catalytically hydrogenated. There is apparently a prejudice against this means of reduction, since even though a large number of reducing agents have been proposed for this purpose (Houben-Weyl, loc. cit. 180 to 223), catalytic hydrogenation has not been considered, presumably because reducing agents which can convert a nitro group into the amino group cleave aromatic hydrazo compounds to give the amines (Houben-Weyl, 11/1, 522). Thus hydrazobenzene in the presence of palladium black, even in the absence of hydrogen, disproportionates to give aniline and azobenzene. Hydrogenation in the presence of nickel produces aniline in virtually quantitative yield. Under the same conditions, phenylhydrazine readily decomposes to give aniline and ammonia (Houben-Weyl, loc.cit. 538).

Thus the invention relates to a process for the preparation of compounds of the general formula I

$$R_n Ar—NH—NH—SO_3 M \quad (I)$$

in which Ar represents an aromatic isocycle or heterocycle, R represents identical or different alkyl, aryl, amino, hydroxyl, alkoxy, aryloxy, halogen, nitro, acylamino, carbamoyl, alkylcarbamoyl, arylcarbamoyl, dialkylamino, arylamino, sulfo or sulfamoyl, M represents hydrogen, alkali metal or one equivalent of alkaline earth metal and n represents 0 or a whole number from 1 to 5, by reduction of compounds of the general formula II

$$R_n Ar—N{=}N—SO_3 M \quad (II)$$

in which Ar, R, M and n have the abovementioned meanings, in a solvent, which comprises carrying out the reduction with hydrogen in the presence of transition metal catalysts.

An advantage of the process according to the invention is that the catalytic hydrogenation can be carried out very selectively, so that, for example, nitro groups in the precursor of the formula II can be retained or converted into amino groups as desired. Accordingly, in a preferred embodiment of the invention, at least one radical R is nitro both in the precursor of the formula II and also in the product of the formula I or at least one radical R in the precursor is nitro and at least one radical R in the product is amino.

In general, preferred precursors of the formula II and products of the formula I are those compounds in which Ar represents phenyl, R represents lower alkyl, lower alkoxy, chlorine, bromine, nitro, phenyl, amino, acylamino, in particular alkanoylamino and benzoylamino, carbamoyl, lower dialkylamino, phenylamino, sulfo or sulfamoyl, M represents hydrogen or alkali metal and n represents 0 to 3.

In the following text, preferred embodiments of the process according to the invention are illustrated in more detail:

Suitable transition metal catalysts are the customary hydrogenation catalysts based on the metals nickel, cobalt, platinum, palladium, ruthenium, rhodium or iridium. Platinum and palladium are preferred. These metals are generally employed on a support, for example on carbon, silicon dioxide, aluminum oxide, aluminum silicates, spinels and zeolites. The catalyst for this purpose advantageously contains 0.05 to 10, preferably 0.2 to 5, in particular 0.5 to 2.5, % by weight of metal. However, skeleton catalysts can also be used, for example Raney nickel.

Since both the precursors and also the products are more or less readily soluble in water, water is the preferred reaction medium. In particular cases, watermiscible solvents, for example lower alcohols, such as methanol and ethanol, and also dimethylformamide and N-methylpyrrolidone, or their mixtures with water, are also suitable. It is also possible to hydrogenate the aryldiazosulfonates in suspension in hydrophobic solvents.

The hydrogenation can be carried out both under normal pressure and also under elevated pressure, the rate of reaction increasing with the pressure. In practice, pressures up to 300 bar are suitable, pressures up to 100 bar, and in particular a pressure range from 20 to 60 bar, being preferred.

The temperature can be selected from a wide range. It depends on the stability of the diazosulfonate and on the desired rate of reaction. Advantageously, the reaction temperature is selected so that precursor and product remain in solution. For this reason, in general, the reaction is carried out at temperatures from about 0 to 200° C., preferably 20° to 120° C., in particular at about 30° to 80° C.

In order to obtain a good space-time yield, the concentration of the precursor is selected to be as high as possible and the other parameters are adjusted to suit the stability of the precursor and the solubility of precursor and product.

The process according to the invention can also be carried out continuously.

It is also possible to prepare the precursor in situ, the arylhydrazine-N-sulfonic acids being obtained from the corresponding aromatic amine by diazotization and reaction with sulfite. This process is particularly advantageous when the arylhydrazine-N-sulfonic acid is readily soluble in water. In this process, an aqueous solution of the diazonium salt is preferably brought to reaction with a solution or suspension of an alkali metal or alkaline earth metal sulfite in such a manner that an excess of one of the two reactants during the reaction is largely avoided, for example by adding the diazonium salt solution as rapidly as technically possible to a very rapidly stirred solution or suspension of the sulfite or by continuously metering stoichiometric amounts of the solutions or suspensions of the reactants into a continuous flow mixer and then passing them into a stirrable delay vessel. A process of this type is described in German Offenlegungsschrift No. 31 25 104.

The products can be hydrolyzed to the corresponding arylhydrazine or to its salts in a known manner. When the products are very soluble or difficult to isolate, it is advantageous to carry out this hydrolysis immediately after the process according to the invention without isolating the arylhydrazine-N-sulfonic acid.

In the examples below, data in percent relate to weight unless otherwise indicated.

EXAMPLE 1

Sodium salt of phenylhydrazine-N-sulfonic acid 277 g of 75% pure sodium salt of phenyldiazosulfonic acid (corresponding to 208 g of 100% pure product = 1.0 mole) were dissolved in 700 ml of water at 55° C. The reddish-brown solution was clarified with 5 g of active charcoal and 5 g of sodium carbonate (anhydrous) were added.

Hydrogenation was carried out under 20 to 40 bar pressure of hydrogen at 80° C. with the addition of 5 g of platinum on carbon (5 % platinum) until no further decrease in pressure was detected. This was the case after about 10 minutes. The hydrogenated, pale yellowish solution was filtered off from the catalyst with suction at 80° C. and 100 g of sodium chloride were added. The product which was salted out was filtered off with suction at +5° C. and dried. 217 g of sodium salt of phenylhydrazine-N-sulfonic acid were obtained, having a purity of 89%, corresponding to 92% of theory.

EXAMPLE 2

Phenylhydrazine hydrochloride

This example illustrates how the phenylhydrazine-N-sulfonic acid produced was hydrolyzed to the salt of the phenylhydrazine.

550 g of sodium salt of phenyldiazosulfonic acid, having a purity of 82.8% (corresponding to 455 g of 100% pure product = 2.19 mole), were dissolved in 2.8 l of water at 40° C. and the reddish-brown solution was clarified with 10 g of active charcoal. The solution, which had a pH of 10, was hydrogenated under 40 bar pressure of hydrogen at 40° C. with the addition of 5 g of platinum catalyst (5% platinum on carbon), until no further decrease in pressure was detected. This was the case after about 10 minutes. After filtering off the catalyst with suction, 400 g of 30% strength hydrochloric acid were added to the filtrate (2.85 l) and 1.5 l of water were distilled off in the course of 1 hour. After cooling down to 5° C., the precipitate was filtered off with suction. 348 g of phenylhydrazine hydrochloride were obtained, having a purity of 81%, corresponding to 89% of theory.

EXAMPLE 3

Sodium salt of p-methoxyphenylhydrazine-N-sulfonic acid 120 g of sodium salt of p-methoxyphenyldiazosulfonic acid, purity 99.2%, and 5 g of sodium carbonate (anhydrous) were dissolved in 300 ml of water at 80° C. and clarified with 5 g of active charcoal. The clarified solution was hydrogenated in the presence of 5 g of Raney nickel under 40 bar pressure of hydrogen at 30 to 40° C. The theoretical amount of hydrogen was consumed. The mixture was heated until the hydrazosulfonate produced had gone into solution and then the catalyst was filtered off with suction. After cooling the filtrate down to 5° C., 40 g of white dry hydrazosulfonate were obtained on filtering off with suction. The mother liquor was evaporated to dryness under water-pump vacuum. By this means, a further 68.6 g of beige-brownish hydrazosulfonate could be obtained. The total yield was 108.6 g of sodium salt of p-methoxyphenylhydrazine-N-sulfonic acid, having a purity of 99.5%, corresponding to 90% of theory.

If a nickel support catalyst is used instead of the Raney nickel, it is necessary to heat the batch to about 80° C. in order to initiate hydrogenation.

EXAMPLE 4

Sodium salt of p-nitrophenylhydrazine-N-sulfonic acid

This example illustrates how the azo group was selectively hydrogenated without the nitro group being attacked.

132 g of sodium salt of p-nitrophenyldiazosulfonic acid (purity 97%) and 300 ml of water were hydrogenated at room temperature in a 1 l autoclave in the presence of 5 g of sulfited platinum catalyst (5% platinum on carbon, according to Example 1 of U.S. Pat. No. 3,803,054. During this, the temperature rose to about 40° C. 11.1 l of hydrogen (calculated for 0° C., 0.49 mole) were absorbed. After the hydrogenation, the catalyst was filtered off hot with suction and the filtrate was stirred until cold. 79 g of sodium salt of p-nitrophenylhydrazine-N-sulfonic acid were obtained, having a purity of 96.5%, corresponding to 60% of theory.

EXAMPLE 5

Sodium phenylhydrazine-2,4,$\beta$-N-trisulfonate

This example illustrates how the aryldiazosulfonate can be prepared in situ and reacted.

127 g of 2,4-anilinedisulfonic acid (0.5 mole) were dissolved in 500 ml of hot water and clarified with 5 g of active charcoal. 10 g of 31% strength hydrochloric acid were added to the filtrate and this was cooled down to 0° to 5° C. The white slurry obtained was diazotized at this temperature with 88 g of 40 % strength sodium nitrite solution. The reaction mixture was tipped as rapidly as possible into a well-stirred mixture of 69 g of sodium sulfite, 15 g of 33% sodium hydroxide solution and 200 ml of water. The pH was decreased from 14 to 9.2 by this means. After stirring for a further 2 hours, the mixture was again clarified with active charcoal and the filtrate was hydrogenated in the presence of 3 g of platinum on carbon (5% platinum) under hydrogen at about 40 bar and at 25° to 30° C. The calculated amount of hydrogen was absorbed. After filtering off the catalyst with suction, the filtrate was evaporated in vacuo. 184 g of sodium phenylhydrazine-2,4,β-N-trisulfonate were obtained (89% of theory).

EXAMPLES 6 to 23

General procedure for the process 1 mole of sodium aryldiazosulfonate (which should be free of decomposition products of the diazonium salt solution, because these can adversely affect the activity of the catalyst) was suspended in 100 ml of water in a hydrogenator having a lifting agitator. 5 g of platinum catalyst (5 % platinum on carbon) were added and 60 bar of hydrogen were introduced. Hydrogenation was then carried out at about 20° to 60° C. until no further hydrogen was absorbed. After releasing the remaining pressure, the gas space of the autoclave was flushed with nitrogen and heated under nitrogen, with stirring, to 80° to 90° C. In general, the arylhydrazine-N-sulfonic acid salt produced went into solution. The solution was expelled from the autoclave by applying pressure and filtered off from the catalyst with suction. If appropriate, the necessary amount of sodium chloride was added to the warm filtrate and this was stirred until cold. The precipitated product was filtered off at +5° C. with suction and dried.

It was sometimes necessary to change to some extent the amount of water, depending on the solubility of the product. In the case of p-phenylaminophenylhydrazosulfonate, the catalyst was advantageously extracted by boiling several times with the mother liquor.

The following compounds were obtained by this procedure:

| Example | Product | Molecular weight | Yield % of theory |
|---|---|---|---|
| 6 | CH₃O—⟨⟩—NH—NH—SO₃Na | 240 | 91 |
| 7 | Cl—⟨⟩—NH—NH—SO₃Na | 244.5 | 83 |
| 8 | CH₃—⟨⟩—NH—NH—SO₃Na | 224 | 90 |
| 9 | ⟨⟩—NH—NH—SO₃Na (CH₃ ortho) | 224 | 88 |
| 10 | ⟨⟩—NH—NH—SO₃Na (CH₃ meta) | 224 | 83 |
| 11 | ⟨⟩—NH—NH—SO₃Na (OCH₃) | 240 | 85 |
| 12 | Cl₂—⟨⟩—NH—NH—SO₃Na | 279 | 79 |
| 13 | (CH₃)₂—⟨⟩—NH—NH—SO₃Na | 238 | 90 |
| 14 | (CH₃)₂—⟨⟩—NH—NH—SO₃Na | 238 | 71 |
| 15 | ⟨⟩—NH—⟨⟩—NH—NH—SO₃Na | 292 | 75 |
| 16 | O=C(NH)(NH)—⟨⟩—NH—NH—SO₃Na | 266 | 85 |
| 17 | NaO₃S—⟨⟩—NH—NH—SO₃Na | 312 | 90 |
| 18 | O₂N—⟨⟩—NH—NH—SO₃Na | 255 | 60 |
| 19 | H₂N.OC—⟨⟩—NH—NH—SO₃Na | 253 | 80 |
| 20 | ⟨⟩—NH—NH—SO₃Na (Cl) | 244.5 | 88 |
| 21 | (CH₃)₂N—⟨⟩—NH—NH—SO₃Na | 253 | 70 |
| 22 | ⟨⟩—NH—NH—SO₃Na (Cl) | 244.5 | 76.1 |
| 23 | Cl—⟨⟩(OCH₃)₂—NH—NH—SO₃Na | 304.5 | 82 |

I claim:
1. A method for making an arylhydrazosulfonate of the formula

$$R_nAr—NH—NH—SO_3M,$$

wherein
Ar is an aromatic isocycle or heterocycle,
R is the same or different alkyl, aryl, amino, hydroxyl, alkoxy, aryloxy, halogen, nitro, acylamino, carbamoyl, alkylcarbamoyl, arylcarbamoyl, dialkylamino, arylamino, sulfo, or sulfamoyl,
M is hydrogen, an alkali metal, or one equivalent of an alkaline earth metal, and n is 0 or an integer from 1 to 5, which method comprises reducing an arylazosulfonate of the formula $$R_nAr-N=N-SO_3M$$

with hydrogen in a solvent in the presence of a transition metal catalyst.

2. A method as in claim 1 wherein

Ar is phenyl,

R is lower alkyl, lower alkoxy, chlorine, bromine, nitro, phenyl, amino, acylamino, carbamoyl, lower dialkylamino, phenylamino, sulfo, or sulfamoyl, M is hydrogen or an alkali metal, and n is 0 or an integer from 1 to 3.

3. A method as in claim 1 wherein at least one R in each of said arylazosulfonate and said arylhydrazosulfonate is nitro.

4. A method as in claim 1 wherein at least one R in said arylazosulfonate is nitro and at least one R in said arylhydrazosulfonate is amino.

5. A method as in claim 1 wherein said transition metal catalyst is a metal of the 8th sub-group of periodic system, on a support.

6. A method as in claim 1 wherein said solvent is water or a water-miscible solvent.

7. A process as in claim 1 performed under a pressure up to 300 bars and at a temperature from 0° to 200° C.

8. A method as in claim 1 performed under a pressure up to 100 bars and at a temperature from 20° to 120° C.

9. A method as in claim 1 performed under a pressure from 20 to 60 bars and at a temperature from 30° to 80° C.

10. A method as in claim 1 performed continuously.

* * * * *